United States Patent [19]
Dell et al.

[11] Patent Number: 4,900,557
[45] Date of Patent: Feb. 13, 1990

[54] PELLET FORMULATION

[75] Inventors: Hans-Dieter Dell, Bergisch-Gladbach; Reinhold Kraus, Koeln; Detlef Schierstedt, Augustin, all of Fed. Rep. of Germany

[73] Assignee: Troponwerke GmbH & Co. KG, Koeln, Fed. Rep. of Germany

[21] Appl. No.: 286,421

[22] Filed: Dec. 19, 1988

Related U.S. Application Data

[60] Continuation of Ser. No. 919,744, Oct. 16, 1986, abandoned, which is a division of Ser. No. 765,907, Aug. 14, 1985, abandoned.

[30] Foreign Application Priority Data

Aug. 30, 1984 [DE] Fed. Rep. of Germany ....... 3431861

[51] Int. Cl.$^4$ .......................... A61K 9/22; A61K 9/52
[52] U.S. Cl. .................................... 424/452; 424/457; 424/458; 424/462; 424/465; 424/468; 424/482
[58] Field of Search ............... 424/452, 457, 458, 461, 424/462, 465, 468, 482

[56] References Cited

U.S. PATENT DOCUMENTS

| | | | |
|---|---|---|---|
| 2,801,203 | 7/1957 | Leb et al. ................................. | 424/4 |
| 3,017,329 | 1/1962 | Dulmage ................................. | 424/4 |
| 3,056,724 | 10/1962 | Marston ................................. | 424/22 |
| 3,341,417 | 9/1967 | Sinaiko ................................. | 424/4 |
| 3,444,290 | 5/1969 | Wai ......................................... | 424/4 |
| 4,193,985 | 3/1980 | Bechgaard ............................ | 424/35 |
| 4,339,463 | 7/1982 | Takagisai ............................... | 424/4 |
| 4,572,833 | 2/1986 | Pedersen et al. .................... | 424/467 |
| 4,574,080 | 3/1986 | Ruswall et al. ...................... | 424/458 |
| 4,713,248 | 12/1987 | Kjornaes et al. .................... | 424/464 |

FOREIGN PATENT DOCUMENTS

| | | |
|---|---|---|
| 0080341 | 6/1983 | European Pat. Off. . |
| 42-25410 | 12/1967 | Japan ................................... 424/4 |
| 44-10799 | 5/1969 | Japan ................................... 424/4 |
| 44-27839 | 11/1969 | Japan ................................... 424/4 |
| 48-24246 | 7/1973 | Japan ................................... 424/4 |
| 49-30526 | 3/1974 | Japan ................................... 424/4 |
| 54-138128 | 10/1979 | Japan ................................... 424/4 |

OTHER PUBLICATIONS

Bechgaard Distribution of Pellets in the Gastrointestinal Tract, the Influence on Transit Time Exerted by the Density or Diameter of Pellets. J. Pharmac., 1978, 30, 690 to 692.

Primary Examiner—Shep K. Rose
Attorney, Agent, or Firm—Sprung, Horn, Kramer & Woods

[57] ABSTRACT

The invention relates to pellet formulations which (a) contain at least one active compound, one binder and one weighting agent, (b) are coated with a lacquer which is resistant to gastric juice or have been granulated in the presence of a lacquer which is resistant to gastric juice, it being possible, if appropriate, for the granules to be coated with a lacquer which is resistant to gastric juice, (c) have an apparent density of 1.4 to 2.4 and (d) have a diameter of 0.2 to 1.8 mm.

7 Claims, 2 Drawing Sheets

PELLET FORMULATION

This is a continuation of Ser. No. 919,744, filed 10/16/86, now abandoned, which is a divisional of Ser. No. 765,907, filed 8/14/85, now abandoned.

The invention relates to pellet formulations with an increased apparent density, tablets and capsules containing such pellet formulations, and processes for the preparation of the pellet formulations.

The aim of developing a pharmaceutical sustained release product is to reduce peak blood level values and to increase the time in which the active compound concentration is in the therapeutic range. Such a presentation form has the advantage that side effects based on increased peak blood level values are reduced and the intervals between taking of the medicament are increased.

Not every medicinal substance is equally suitable for application of conventional sustained release methods. For example, if a medicinal substance is chiefly adsorbed in the stomach and in the first sections of the intestine (R. Gröning, Pharm. *Ind.* 46, page 89, 1984) ("Limited absorption"), conventional sustained release methods fail. In such a case, in vitro sustained release manifests itself in vivo only by a reduction in bioavailability (see FIGS. 1 and 2).

Such a substance could be released in a sustained manner only if the residence time in the gastrointestinal tract, in particular in the stomach, were increased. This can be effected, for example, by increasing the density. U.S. Pat. No. 4,193,985 describes, for example, a formulation which consists of pellets of increased density with an insoluble diffusion membrane. The release profile of such a system is chiefly intended for the small intestine. Since the residence times in the small intestine vary due to many factors, such a principle cannot be applied to medicinal substances which are absorbed only in relatively short gastrointestinal sections.

Surprisingly, it has been found that pellets of increased density which are lacquered with a coating which is resistant to gastric juice are outstandingly suitable for sustained release of substances of limited absorption. [An in vivo comparison with a pellet formulation resistant to gastric juice and acemetacin which is not in sustained release from on two healthy volunteers shows a shift in the blood level maximum from about 4 to about 8 hours without a reduction in the relative bioavailability (see FIG. 3).]

The invention thus relates to pellet formulations which are characterized in that they (a) contain at least one active compound, one binder and one weighting agent, (b) are coated with a lacquer which is resistant to gastric juice or have been granulated in the presence of a lacquer which is resistant to gastric juice, it being possible, if appropriate, for the granules to be coated with a lacquer which is resistant to gastric juice, (c) have an apparent density of 1.4 to 2.4 and (d) have a diameter of 0.2 to 1.8 mm.

The apparent density is preferably 1.5 to 1.8, and particularly preferably 1.6.

The pellet formulations can contain 0.1 to 80% by weight of active compound. The weighting agent is present in concentrations of 20 to 98% by weight, and the remainder (to make up to 100% by weight) consists of binder and other additives, such as disintegrating agents and the like, percentages relating to the non-lacquered pellet.

The density of the pellet formulation can be established by substances of high specific gravity, such as $TiO_2$, $BaSO_4$, ferrum reductum and iron oxides. The weighting agents are preferably employed in amounts of 40 to 70% by weight, based on the non-lacquered pellet.

The size (diameter) of the pellets according to the invention is 0.2 to 1.8 mm, preferably 0.8 to 1.5 mm and particularly preferably 0.5 to 1.25 mm.

If the pellets are combined with an initial dose, a sustained release product which completely fulfils the above mentioned desired properties is obtained.

The pellet formulations can be pressed to tablets or filled into capsules. This can be effected at the same time as an addition of the free active compound which acts as the initial dose. The initial dose, which is added as a powder, if appropriate with other additives, but also in other than powder form, is preferably 10 to 60% by weight, based on the total weight of the active compound. $\frac{1}{3}$ of the total dose is particularly preferably employed as the initial dose. If therapeutically desirable, the pure pellet formulation can also be used.

As already mentioned, the sustained release method according to the invention is suitable for medicinal substances which display "limited adsorption". This method can also be of advantage for substances which do not display these adverse properties, since the expenditure on development is considerably curtailed. For example, it is not necessary to optimize the in vitro solution rate by in vivo experiments. In a preliminary in vivo experiment, it is merely necessary to test the pure pellet formulation which is resistant to gastric juice against the corresponding commercial product. From these blood level values, it is then possible to calculate the ratio between the dose which is resistant to gastric juice and the initial dose.

Preferred active compounds for the pellet formulations according to the invention are acemetacin (60 to 200 mg), diclofenac (70 to 220 mg), indometacin (60 to 180 mg) or nifedipine (10 to 60 mg), and if appropriate salts thereof. The preferred amounts are given in parentheses.

In principle any lacquer which leads to film coatings which are resistant to gastric juice, for example cellulose acetate phthalate, hydroxypropylmethyl-cellulose phthalate and other cellulose phthalate derivatives, polymers of methacrylic acid and methacrylic acid esters (Eudragit ®L and S) and a methacrylic acid/methyl acrylate copolymer (Eudragit ®L 30 D) can be used for lacquering the pellets.

The apparent density of the pellet formulations can be determined pygnometrically with a suspending agent in which the lacquer coating is insoluble.

The pellet formulations are prepared by mixing the active compound with the weighting agent and, if appropriate, the binder and then pelleting or granulating.

Granulation is effected, for example, by the methods described in "Ullmann, Volume 18, Pharmazeutische Technologie" (Pharmaceutical Technology)".

MOIST GRANULATION

In moist granulation, the powder mixture is processed with a liquid to a paste, from which the granules are formed, after drying, evaporation or solidification of the granulation liquid. A differentiation is made between:

(a) Build-up Granulation

The powder mixture is kept in motion and is brought to the desired granule size by spraying with granulation liquid.

In the plate granulation process, the powder mixture to be granulated is introduced onto a plate rotating at an angle. The granules formed are spherical. In fluidized bed granulation, the powder mixture is whirled up in a stream of air, kept in suspension and sprayed with the granulation liquid. In this case also, substantially spherical granule grains are formed.

(b) Breaking-down Granulation

The powder mixture is thoroughly uniformly moistened with the granulation liquid by kneading with a kneader and is pressed, in paste consistency, through a sieve or a perforated roll or perforated disc. After drying, the cylindrical or parallelepipedal granules are sieved out, if appropriate, to the desired particle size.

The granulation liquid used is, depending on the solubility of the active compound, preferably water, and in addition, for example, water/alcohol mixtures or solutions of binders. Suitable binders are macromolecular substances, such as cellulose derivatives, gelatin, starch, polyvinylpyrrolidone or alginates.

MELT GRANULATION

Sinter or melt granules are formed by melting constituents of the powder mixture and shaping them through a sieve.

DRY GRANULATION

In dry granulation, the powder mixture is shaped into relatively large, coarse pressed pieces, so-called briquettes, in tabletting machines or mills, and are coarsely comminuted and sieved to the desired granule size. The process is particularly used in processing active compounds which are unstable to heat or sensitive to moisture.

To prepare tablets containing the pellet formulations according to the invention, the usual tabletting processes are resorted to (see, for example, Ullmann, Volume 18, Pharmazeutische Technologie (Pharmaceutical Technology)).

During tabletting, the pellet formulation or granule formulation is converted into a compressed tablet by applying a high pressure, if appropriate in the presence of free active compound and other additives (initial dose). By combination with corresponding auxiliaries, almost any active compound can be converted into a tablet which, in addition, can also have certain properties necessary for its use.

The galenical properties of tablets, in particular their disintegration in water or in digestive juices and their mechanical characteristics are decided by the amount and the physico-chemical properties of the active compounds and auxiliaries, in addition to the production process.

Auxiliaries for the production of tablets are classified into the following most important types:

Fillers, for example lactose and sucrose

Binders, for example starch, gelatin, sugar, cellulose ethers and polymers, for example polyvinylpyrrolidone disintegrating agents, for example starch, starch ethers and Kollidon®CL Lubricants and mold release agents, for example talc, stearates and silicones Flow control agents, for example highly disperse silicon dioxide and talc.

Capsules can likewise be produced by methods, which are described in "Ullmann, Volume 18, Pharmazeutische Technologie" (Pharmaceutical Technology), using pellet formulations according to the invention.

By varying the binder, the binder concentration in the pellets or granules and the production process, it is possible to control the dissolution time for the pharmaceutical active compound in the small intestine.

If, for example, rapid disintegration in the small intestine is desired, it is possible to add, if appropriate, a disintegrating agent, such as Kollidon®CL, starch, UAP, Avicel® and the like, or a disintegration accelerator, such as Aerosil®, surfactants and the like. (Kollidon®CL=crosslinked polyvinylpyrrolidone, UAP-=ultraamylopectin, Avicel®=microcrystalline cellulose and Aerosil®=highly disperse $SiO_2$).

The lacquering which is resistant to gastric juice can be applied by the customary lacquering processes, such as, for example, in a fluidized bed or an open or closed kettle system.

EXAMPLES

The initial dose, in the form of a powder mixture or as tablets together with the pellets which are resistant to gastric juice, can be filled into capsules (for example 10 to 60% initial dose, preferably ⅓ of the total dose).

The time t in hours is plotted on the x-axis in the figures.

In FIGS. 2, 3 and 4, the blood level value is given in μmol/l on the y-axis.

FIG. 1 shows the "in vitro" release of acemetacin from acemetacin diffusion pellet formulations (B, C, D, E, F) and acemetacin which is not in sustained release form (A). USP paddle/900 ml of artificial gastric juice, 100 revolutions/minute.

FIG. 2 shows a blood level comparison of acemetacin and acemetacin diffusion pellet formulations. Curve A relates to a commercial acemetacin product. Curves B, C and F describe sustained release experiments according to the prior art. Dose: in each case 120 mg of acemetacin.

| Recipes of weighted pellets which are resistant to gastric juice | | | | | | | | | |
|---|---|---|---|---|---|---|---|---|---|
| | Indometacin | | Diclofenac | | Nifedipine | Acemetacin | | Acemetacin | Acemetacin |
| Active compound | 60 | 60 | 60 | 60 | 60 | 60 | 60 | 60 | 60 |
| Titanium dioxide | 80.0 | 94.5 | 78.0 | 93 | 260.0 | 75.6 | 94 | | 94 |

| | Recipes of weighted pellets which are resistant to gastric juice | | | | | | | | |
|---|---|---|---|---|---|---|---|---|---|
| | Indometacin | | Diclofenac | | Nifedipine | Acemetacin | | Acemetacin | Acemetacin |
| Iron oxide (black) | | | | | | | | 74.3 | |
| Corn starch | | | | | 150.0 | | | | |
| Kollidon ® CL | 7.8 | | 7.9 | | 9.0 | 7.8 | | 7.8 | |
| Kollidon ® 25 | 14.3 | 13.4 | 14.6 | 13.7 | 59.8 | 14.4 | 13.6 | 14.0 | 13.6 |
| Celluloseacetate phthalate | 20.5 | 20.5 | 20.5 | 20.5 | 52.5 | 20.5 | 20.5 | 20.5 | |
| Eudragit ® L 30 D | | | | | | | | | 30.0 |
| Talc | 1.0 | | 1.0 | 1.0 | 3.0 | 1.0 | 1.0 | 1.0 | 3.0 |
| Triacetin | 4.6 | | 4.6 | 4.6 | 13.8 | 4.6 | 4.6 | 4.6 | |
| PEG 6000 ® (polyethylene glycol) | | | | | | | | | 3.0 |

IN VIVO INVESTIGATIONS

It was possible to demonstrate the sustained release effect in vivo by human studies which in comparison with the active compound acemetacin not in sustained release form, in the form of the commercial product Rantudil ®.

Figure 1:
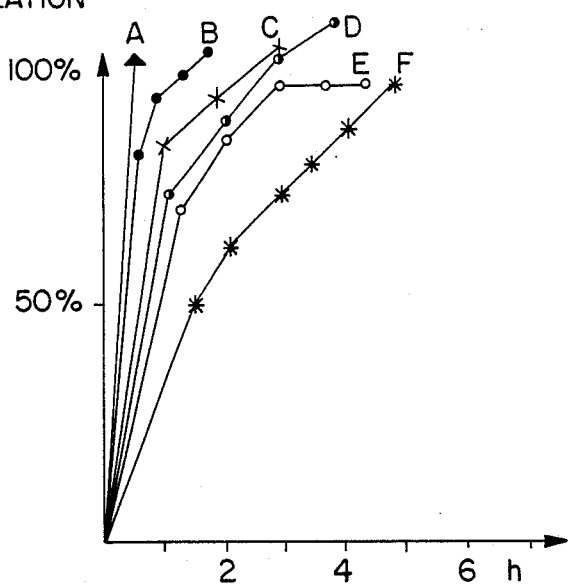
Figure 2:
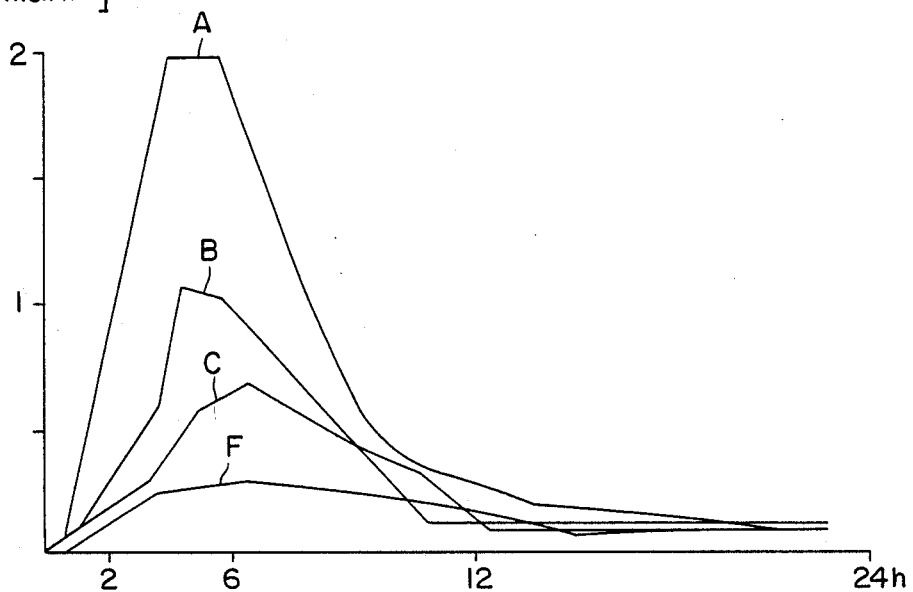
Figure 3:
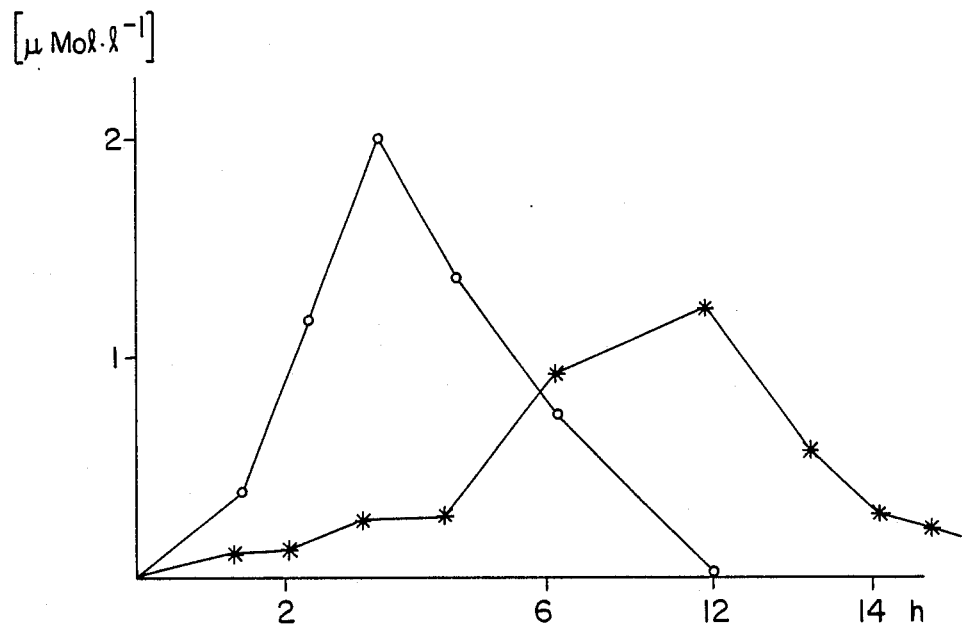
FIG. 3 shows a blood level comparison on two volunteers. [An in vivo comparison with a pellet formulation which is resistant to gastric juice and acemetacin which is not in sustained release form on two healthy volunteers shows a shift in the blood level maximum from about 4 to about 8 hours without a reduction in the relative bioavailability (see FIG. 3).]
Figure 4:
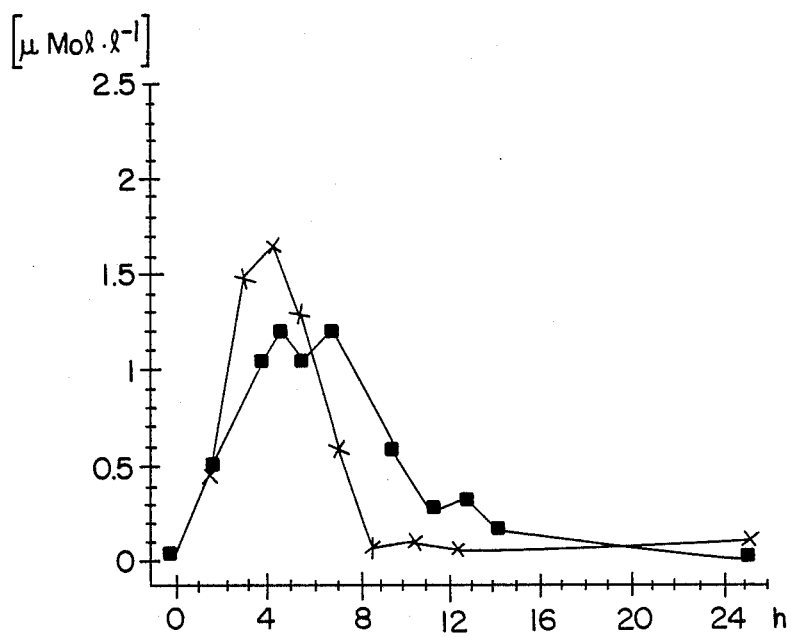
FIG. 4 shows the blood level course after administration of acemetacin: boxes=sustained release formulation, crosses=normal form (not sustained release), mean value (n=4); amount administered=90 mg of active compound.

In FIG. 4, the shape of the mean value curves for the various courses of the blood level curves can be seen (4 volunteers).

The effect of the sustained release formulations (according to J. Meier, E. Nulsch and R. Schmidt, Eur. J. Clin. Pharmacol. 7, 429, 1974, P. Guissou, G. Guisinaud, G. Llorca, E. Lejeune and J. Sasard, Eur. J. Clin. Pharmacol. 24, 667, 1983 and R. Verbesselt. T. B. Tjandramaga, A. Mullier, P. J. De Schepper, T. Cook, C. Derouwaux, R. Kramp and S. Hwang, Eur. J. Clin. Pharmacol. 24, 563, 1983) were investigated comparatively in a randomized cross-over experiment on a larger number of volunteers.

The sustained release formulation proved to be a true sustained release product in respect of the time of the maximum blood level ($t_{max}$), the maximum blood level concentration ($C_{max}$), the blood level ($\mu mol/l$) at various times after administration, the absorption half-life, the residence time and the retard quotient. The differences from the product which is not in sustained release form are statistically confirmed.

The following example illustrates one manner of producing filled gelatin capsules in accordance with the present invention:

EXAMPLE

The following components are used for the non-coated granules:

| | | |
|---|---|---|
| I | acemetacin | 60.0 mg |
| | titanium dioxide | 75.6 mg |
| | collidone CL | 7.8 mg |
| II | collidone 25 (solution) | 14.4 mg |

The coating, which is resistant to gastric juice, consists of the following constituents:

| | | |
|---|---|---|
| III | cellulose acetate phthalate | 20.5 mg |
| | triacetin | 4.6 mg |
| | talcum | 1.0 mg |

Components I are mixed in a rapid mixer for 2 minutes (286 r.p.m). Then solution II is added in one pouring while the mixer is in operation (about 2 minutes).

The moist composition is granulated with a breaker plate granulator (hole size: 1.5 mm) and dried at 50° C. Then the granules are comminuted through a 1 mm screen and the dust constituents are separated off.

The granules are coated in a fluidized-bed granulator. The components III are sprayed, in a 10% acetone solution (relative to the cellulose acetate phtalate), and to the granules in the fluidized bed. Uniform pellets of the active compounds are obtained in this way.

The pellets are then filled into yard gelatin capsules.

It will be understood that the specification and examples are illustrative but not limitative of the present invention and that other embodiments within the spirit and scope of the invention will suggest themselves to those skilled in the art.

What is claimed is:

1. A sustained release formulation comprising pellets
   (a) containing acemetacin and at least, one binder, one weighting agent and one disintegrant,
   (b) coated with a lacquer which is resistant to gastric juice or granulated in the presence of a lacquer which is resistant to gastric juice, and
   (c) having an apparent density of 1.4 to 2.4 and having a diameter of 0.2 to 1.8 mm and an initial dose of acemetacin which comprises 10 to 60% by weight, based on the total weight of the acemetacin of the pellet in free form.

2. A sustained release formulation according to claim 1, wherein the pellets contain 0.1 to 80% by weight of acemetacin, 20 to 98% by weight of weighting agent and binder to make up 100% by weight, based on the pellet excluding lacquer.

3. A sustained released formulation according to claim 1, containing at least one of $TiO_2$, $BaSO_4$, iron oxide and ferrum redactum as the weighting agent.

4. A sustained released formulation according to claim 1, containing 40 to 70% weighting agent, based upon the pellet excluding lacquer.

5. A sustained release formulation according to claim 1, wherein the pellets have an apparent density of 1.5 to 1.8.

6. Capsules or tablets made up of the sustained release formulation according to claim 1.

7. Capsules or tablets according to claim 1, each containing 60 to 200 mg of acemetacin.

* * * * *